United States Patent [19]

Cook

[11] 4,002,760
[45] * Jan. 11, 1977

[54] TREATMENT OF HUMANS WITH CHOLINESTERASE REACTIVATORS

[76] Inventor: Albert W. Cook, Centre Island Road, Centre Island, N.Y. 11771

[ * ] Notice: The portion of the term of this patent subsequent to Dec. 23, 1992, has been disclaimed.

[22] Filed: Nov. 24, 1975

[21] Appl. No.: 634,794

Related U.S. Application Data

[63] Continuation-in-part of Ser. No. 482,061, June 24, 1974, Pat. No. 3,928,594.

[52] U.S. Cl. .................................................. 424/263
[51] Int. Cl.$^2$ ........................................ A61K 31/44
[58] Field of Search ..................................... 424/263

[56] References Cited

UNITED STATES PATENTS

| | | | |
|---|---|---|---|
| 2,816,113 | 12/1957 | Wilson et al. | 424/263 |
| 2,996,510 | 8/1961 | Green | 424/263 |
| 3,063,901 | 11/1962 | O'Leary | 424/263 |
| 3,077,476 | 2/1963 | Hackley et al. | 424/263 |

OTHER PUBLICATIONS

New Drugs, (1966), pp. 537–539.
Goodman et al., The Pharmacological Basis of Therapeutics, (1966), pp. 413–414, 454–455.
Merck Manual (1972), 12th Edition, pp. 1304–1305.

*Primary Examiner*—Norman A. Drezin
*Attorney, Agent, or Firm*—Nolte and Nolte

[57] ABSTRACT

Cholinestrase reactivators are administered to treat the pain of tic douloureux.

2 Claims, No Drawings

TREATMENT OF HUMANS WITH CHOLINESTERASE REACTIVATORS

This is a continuation-in-part of application Ser. No. 482,061, filed June 24, 1974, now U.S. Pat. No. 3,928,594.

This invention relates to new therapeutic uses of cholinesterase reactivators for the symptoms and signs associated with demyelinating processes or hypercholinergic or other conditions in man characterized by defective neural transmission in association with an acetylcholine-cholinesterase imbalance due to relative decrease in choinesterase activity.

Cholinesterase reactivators such as 2-PAM (2-formyl-1-methylpyridium oxime or pralidoxime) and salts thereof such as 2-PAM-Cl, 2,3-butanedione-2-oxime (DAM), other 2-oxooximes, pyruvaldehyde aldoxime (MINA) and bis quaternary pyridine aldoxime (TMD-4), were originally developed as antidotes for acute nerve gas poisoning and other exogenous organic phosphorous compounds acute poisoning, such as from insecticides. They have found limited usefulness as secondary compounds to be employed in the treatment of patients with Myasthenia gravis in which there had been a crisis produced by primary drugs. The principal action of cholinesterase reactivators is felt to be the reactivation of the enzyme cholinesterase.

According to the present invention, new therapeutic uses are provided for cholinesterase reactivators, including treatment of the symptons and signs of diseases and other conditions in man which, it is believed, are associated with demyelination as well as other conditions in man characterized by acetylcholine-cholinesterase imbalance due primarily to relative decreased cholinesterase activity and, therefore, defective neural transmission. It is to be understood that the prior art did not recognize any major utility for cholinesterase reactivators apart from the treatment of exogenous phosphorous compounds acute poisoning. Though the use of cholinesterase reactivators for the treatment of exogenous phosphorous compounds acute poisoning has been known for many years, no one had heretofore proposed the use of cholinesterase reactivators for the purposes disclosed in my present patent application.

Cholinesterase has been identified as true cholinesterase or acetylcholinesterase (ACHE) and pseudo or plasma cholinesterase (CHE). The former is distributed throughout various segments of the autonomic, peripheral and central nervous systems and also in other systems outside the nervous systems and is felt to be associated with membrane phenomena. Pseudo cholinesterase is also distributed throughout the nervous system and is believed to be primarily in myelin and the glial supporting cells (oliogodendroglia). CHE is also distributed throughout various tissues outside the nervous system.

The prime function of cholinesterases in the nervous system is to create the hydrolysis of the protein ester acetylcholine (ACH). Electrical activity of neural tissue is intimately related to ACH and cholinesterases. The precise duration in which ACH is permitted to act is regulated by the timed destruction of ACH by the cholinesterases.

It is known that ACH has various actions described as muscarinic and nicotinic and also central actions in terms of impulse propagation along axons (axon potential) and possibly as a transmitter at some synaptic sites. It is felt by some also that there may be a muscarinic type action in the central nervous system. The precise mechanism of these actions is unknown, but it is related intimately to receptor sites. In the proper amounts, ACH facilitates transmission at these points and in large amounts or when present over longer periods, it inhibits neural function. It has been shown that electrical activity in neural tissues ceases with the absence of cholinesterase because of the failure to destroy ACH which then creates a state of hyperpolarization. In sum, there is a dynamic relationship in terms of function of neural tissue which is related to the proper balance of ACH and cholinesterase in varied areas of the nervous system.

Demyelinating diseases are associated with pathological processes in which the sheaths of myelin around axons are destroyed wholly or in part. It is known that myelin is a lipoid structure containing various chemical compounds such as cholesterol, phospholipids and galactosphingolipids. There are also present in myelin several types of protein, one being the basic protein. It is known that interference with the structure of myelin primarily produces dysfunction of axon conductivity, although anatomically the axon may appear to be relatively intact. This is so called primary demyelination. In secondary demyelination there is alleged to be a primary disorder in the axon with subsequent myelin degeneration around this axon. There are many clinical syndromes associated with demyelination in the nervous system and the symptoms and signs depend upon the location of the process, namely the axons involved and indeed their failure of conduction. In general, the cause of many demyelinating processes is unknown. It is known that demyelination occurs after a rather characteristic response to many noxious agents affecting the nervous system. These agents can be infectious, traumatic or toxic. The outstanding example of a primary demyelinating disease is multiple sclerosis, and the outstanding example of secondary demyelination is amyotrophic lateral sclerosis or motor neuron disease. In the periphery and centrally, Wallerian degeneration is characteristically a secondary type of demyelination.

I have found that in both categories of demyelinating processes in man electrical stimulation over the dorsum of the spinal cord can reverse or modify many of the symptoms and signs associated with these processes. These include mental deterioration and depression, pain, impaired performance of the voluntary motor system in terms of power and synergy, i.e., abnormal movements, spasticity and peripheral sensory thresholds and, less pronouncedly, cortical seizure activity.

My observations with electrical stimulation in these catagories of demyelinating disease, which also include traumatic situations of the central nervous system, suggest that there is indeed an imbalance in cholinergic and adrenergic activity, namely there is a relative central hypercholinergic state.

I believe that when there is destruction of myelin in varying degrees and also varying degrees of axonal destruction, the symptons and signs are not totally irreversible. This was demonstrated by electrical stimulation over the spinal cord, namely the reversibility of some of the symptoms and signs as enumerated above. It is felt that electrical stimulation reactivates axonal transmission and synaptic function which had been physiologically blocked. It is further felt that this has to do with biochemical events and, of necessity, has to involve the essential elements of acetylcholine and cholinesterase relationships.

I established that in primary and secondary demyelinating disease electrical stimulation could change function and it is known that with demyelination the biochemical substrates in the diseased area are disturbed. Cholinesterase activity has been demonstrated to be significantly modified in the area of the plague in association with varying degrees of demyelination, such as in multiple sclerosis. This would result in a relative excess of acetylcholine and a hypercholinergic state relative to axons and, therefore, a hyperpolarization block of conduction, namely, a functional or neurophysiological block which could be reversed under suitable conditions, endogenous or exogenous.

It is known that excess acetylcholine may act as a persistent cathode and result in hyperpolarization and placement of an anode and subsequent stimulation in that area of membrane will reverse the process, and I perceived a similar situation with stimulation of the spinal cord in man. I have concluded that compounds which activate cholinesterase systems, typically oxime compounds such as, for example, 2-PAM and its salts, DAM, other 2-oxo-oximes, MINA, and bis quaternary pyridine aldoxime (TMB-4) should act to mitigate the signs and symptoms of demyelinating diseases and pathological processes which result in a disturbance in ACH-cholinesterase relationships in terms of relative decreased cholinesterase activity.

Apart from 2-PAM and physiologically acceptable salts thereof, DAM, other 2-oxo-oximes, MINA and bis quaternary pyridine aldoxime (TMB-4), other cholinesterase reactivators that may be used according to the present invention to mitigate the signs and symptoms of the aforementioned diseases and processes are the entire class of oximes disclosed in U.S. Pat. No. 2,816,113, the oximes discussed in U.S. Pat. No. 3,063,901 and the oximes disclosed in U.S. Pat. Nos. 2,996,510 and 3,077,476. In the context of the present invention the cholinesterase reactivators may be administered in any dosage form, for example, orally, intravenously, intramuscularly, intraperitoneally or subcutaneously. Moreover, these compounds may be utilized in the present invention in dosages within limits already established as safe and effective in the treatment of poisoning from exogenous organic phosphorous compounds and in dosages given to normal people for prophylactic purposes when they are about to be possibly exposed or may have been exposed to exogenous organic phosphorous compounds such as in the agricultural or horticultural application of organic phosphorous insecticides.

The herinafter described clinical experiments are illustrative of the present invention.

Initially, 2-PAM-Cl was given parenterally and then orally in single doses of 500 to 1000 mg. to persons afflicted with multiple sclerosis. The time course of the effectiveness of the drug was found to be about 15 to about 30 minutes for changes to appear and the changes gradually disappeared over a period of about one to about two hours. Subsequently, repeated daily doses were given to individual patients at different stages of a demyelinating disease and with different demyelinating diseases. Finally, patients received the drug who (1) never had stimulation of the spinal cord before, (2) had had previous stimulation of the spinal cord, and (3) while stimulation of the spinal cord was being carried out in a partial or complete manner. Similarly, a group of patients were given a placebo. After their reaction to the placebo was observed, some of the same patients were given 2-PAM-Cl. Also, many of these patients had been under observation previously for the effectiveness of another drug, Dantrium, which allegedly modifies spasticity. Observations of the patients to whom a placebo had been given were carried out with and without spinal cord stimulations. Comparative evaluation was therefore permitted.

The results can be summarized as follows:
1. Patients receiving placebo did not show the changes as seen with 2-PAM-Cl.
2. Patients receiving Dantrium did not shown the total effects as seen with 2-PAM-Cl.
3. The administration of 2-PAM-Cl repeated the effects seen with spinal cord stimulation in the same patients but also as seen in others.
4. In many instances of a patient receiving stimulation of the spinal cord, administration of 2-PAM-Cl required that the power delivered by the stimulator be reduced because the drug plus the stimulation aggravated the parathesiae experienced with stimulation alone. The cumulative effect was too strong.
5. Effects observed repeatedly were:
   a. A sense of alertness; abolition of mental depression and abolition of a feeling of fatique which in many of these patients is profound. Improved cerebral or mental function also occurred in those in whom the foregoing was a prominent feature.
   b. Impaired function in the voluntary motor system was much alleviated as would occur with stimulation of the spinal cord.
   c. There was a decrease in ataxia, particularly static postural ataxia, as well as abnormal movements characterized as dystonic or choreic.
   d. There was abolition of visual blurring if this had been present.
   e. There was decreased spasticity and re-operation of reciprocal innervation.
   f. There was relief of pain, if this had been present.
   g. In some, the strength of speech was improved significantly.
   h. Active movements could be carried out for longer periods without fatique and decremental dysfunction.

Adverse effects were transitory and observed in only some patients. These effects included nausea and vomiting, visual blurring, an initial sense of fatique, drying of the mouth and diarrhea.

In some patients I have used both spinal cord stimulation and the cholinesterase reactivator and have found that they complement each other provided that the dosage of the drug and/or the strength of the stimulation delivered are modified when the total effect appears to be too great. In some patients, the drug is simply used alone.

The significant effect in demyelinating diseases of compounds capable of changing the chemical constitution of cholinesterase suggests that a major effect in the symptomotology depends upon the degree of change in the chemistry of cholinesterase. The mitigation of mental deterioration and depression, pain and spasticity, increased function in the voluntary motor system and increase synergy and signs of renewed operation of reciprocal innervation in terms of appropriately timed inhibition and facilitation, i.e., decrease in abnormality or normalizing of movements, all indicate a fundamental modification of a process having to do with neural transmission and synaptic zones and their connections, axons and dendrites. The almost precise repetition of the effect of spinal cord stimulation by the administration of the drug alone and the complementary function of both together suggests also the modification of a basic mechanism, that of ACH-cholinesterase. It is known that these relationships are essential for propagation of the axon potential or neural impulse and also at certain synaptic areas, both peripherally and centrally. This evidence also tends to support the conclusion that cholinesterase reactivators such as 2-PAM-Cl indeed have a very significant action in terms of the central nervous system which prior to this time has not been elucidated completely. In addition, it also emphasizes the significance of biochemical change in the cholinesterase systems in relationship to the central nervous system in patients with primary and secondary demyelinating processes and other aforementioned processes and the modification of such biological change by cholinesterase reactivators. It also indicates that such cholinesterase reactivators are effective in processes of long duration since these patients had been diseased for years. This is in sharp contrast to cases of acute organic phosphorous poisoning. In the latter it is felt treatment must be immediate not only for clinical reasons but also because of aging of the phosphorylated cholinesterase. This does not seem to be the case in my applictions of cholinesterase reactivators.

The details relating to spinal cord stimulation are described in an article authored by myself and a coworker and entitled "Chronic Dorsal Column Stimulation in Multiple Sclerosis," New York State Journal of Medicine, Dec. 15, 1973, pp. 2868–2872.

In further accordance with the present invention, cholinesterase reactivators are adminstered to treat the pain of tic douloureux. It is felt that the facial neuralgia described as tic douloureux is due to an inbalance centrally in ACH relationships. As described above, according to the invention, cholinesterase reactivators are employed in man in primary and secondary demyelinating processes. Multiple sclerosis represents the classical example of a primary demyelinating process. Tic douloureux occurs in 4–5% of patients with multiple sclerosis. In addition, increasingly evidence is accumulating indicating demyelinating changes in roots of V cranial nerves of patients with tic douloureux without multiple sclerosis. In the latter, plagues of dymyelination are in the brain stem. In the former, areas of demyelination are in the roots before entry into the brain stem. Demyelination is viewed as the patho-anatomic counterpart to a dynamic patho-physiological and patho-chemical relationship affecting enzyme systems one of which is that of acetylcholine-cholinesterase. Because of the experience with 2-PAM-Cl in multiple sclerosis and the above background, 2-PAM-Cl was given to patients with tic douloureux with multiple sclerosis and without multiple sclerosis.

The specificity of action of 2-PAM-Cl biochemically and its actions in patients with multiple sclerosis with tic douloureux and with tic douloureux without multiple sclerosis suggests that the concept of a disturbed acetylcholine-cholinesterase relationship has merit both patho-physiologically and therepeutically.

Recently, it has been shown indeed that cholinesterase has the facility to move from one neural structure to another through extra-neural spaces. This occurred particularly around the trigeminal nucleus in the brain stem of lower animals. This provides suggestive evidence that in the area of the central brain stem part of the trigeminal nerve complex, there is indeed the biochemical mechanism to which I allude and which indeed may be intimately associated with electrical phenomena seen in experimental studies relating to trigeminal pain. It tends to support my thinking concerning the relationships between acetylcholine-cholinesterase and tic douloureux and multiple sclerosis and the effect of 2-PAM-Cl, namely, a reactivation of cholinesterase.

When 1 gram of 2-PAM-Cl was administered intravenously, it relieved or modified the pain of tic douloureux in 15 minutes and the effect lasted over 1–2 hours; repeated dosages were given. Maximum doses in three days to one patient totaled 13 grams in a case with severe pain, which relieved the pain. Other patients with less pain require less.

In the patient with severe pain, 13 grams in three days with 7 grams on the third day finally abolished the recurring attacks which had existed for three months. Other drugs, sold under the trademarks Tegretol and Dilantin, had no effect.

In another patient with multiple sclerosis and tic douloureux, 2-PAM-Cl relieved pain but did not abolish it when 2–3 grams were administered each day for 6 days. The problem here may have been lack of sufficient drug to finally abolish bout, although it indeed relieved pain in the time course indicated above.

Electrical stimulation of the nerve directly by percutaneously inserted electrodes stopped the bouts of pain. So again, 2-PAM-Cl and electrical stimulation act the same way.

By way of amplification, tic douloureux is pain that occurs in individual "bouts" over weeks or months. During these episodes, there are repeated individual "attacks" of severe pain. 2-PAM-Cl relieves individual attacks within the time course of the drug. Repeated doses are necessary. A three-month "bout" was abolished by a massive dose of 13 grams in three days and 7 grams the last day. So it appears that large doses are needed for "large pain" and may be necessary to arrest a "bout". Initial electrical stimulation of nerve stops an "attack". If stimulation is discontinued, attacks recur. Prolonged, i.e., a large dose of, stimulation will abolish a "bout"; namely, withdrawal of stimulation after its application for a prolonged period, viz., days, will result in absence of pain for weeks or months. Again, large doses of drug and large doses of stimulation seem to act the same in abolishing "bouts".

In more technical terms, paroxysmal severe lancinating pain in the distribution of the peripheral sensory fibers of the trigeminal complex has been termed tic douloureux.

Clinical characteristics of tic douloureux are:
1. Pain is paroxysmal, lancinating of short duration, restricted to the sensory distribution of the fifth cranial nerve.
2. Stimuli which ordinarily do not evoke pain of any type trigger paroxysms which outlast the duration of the stimulus.
3. Associated with acute paroxysm there may be marked vasodilation on the affected side of the face as well as contraction of the facial muscles on that side.
4. There may be total inability to talk or even move the face at the time of the pain.
5. There exists at times, very focal trigger zones which set off severe generalized paroxysm or just "short jabs."
6. Very often a pathoanatomic cause cannot be identified as associated with the syndrome although it has been found associated with compression of the posterior root from aberant blood vessels crossing the root, tumors in the cerebellar portion angle, elevated petrous ridge on that side, etc.

All these elements suggest that tic douloureux may be associated with compression of some type of the posterior root in the cerebellar pontine angle. In 4–5% of patients with multiple sclerosis, classical tic douloureux occurs. Here there is no compression but "plagues" at the area of the root entry zone or adjacent to the area in the brain stem. In multiple sclerosis patients, there is likely to be bilateral pain in series or even alternating during the same period.

In general, section of the peripheral branch of the sensory root or of the sensory root itself will abolish the pain. This is more likely to be the case with total section of the posterior root. Recurring pair occurs more often in partial section of the posterior root and in peripheral neurectomy whether surgical or chemical. Destruction of fibers of the root system has been done by various means and simply rubbing of the root may result in abolition of attacks.

Customarily it is stated that there are no abnormal neurological signs in the face of these patients in between attacks. However, this requires modification. An almost constant abnormality in my experience is "the smirk" of the face on the side of the pain. Specifically, there is a tendency for the nasal labial fold to be deepened here and that side of the face is mildly "drawn up." This sometimes give the appearance of mild swelling on this side of the face. Interestingly enough, this "smirk" is constantly accentuated after section of the posterior root. To me, it represents change in tonic innervation of the facial musculature. This abnormality exists without pain and is exaggerated at the time of pain paroxysms. So, too, using conventional methods of sensory examination, there will be found no loss or change of sensation over the face on the side of pain. However, if fine graded hairs are employed, it will be found that frequently on the side of the pain there is an elevated threshold to light punctuate touch. Gross testing never elicits this.

Pathoanatomical considerations: It has been demonstrated that simple irrigation of the surface of axons in the spinal cord can result in demyelination. It has also been demonstrated that a focal electrical conduction block is associated with focal areas in demyelination Compressure lesions in the neural axis also result in focal demyelination. It is of interest here that many of the known associated lesions with tic douloureux, BW (petrous ridge) compression, etc., may result in focal partial demyelination of the root. This may or may not result in a demonstrated sensory loss. In multiple sclerosis one of the principle features is that of central demyelination and associated loss of conductance. The operation of rubbing of the trigeminal root undoubtedly increases demyelination of fibers to accomplish more complete lack of conduction in the entire system just as in root section, only here anatomical continuity is destroyed.

More recently evidence has been presented which indicates that in patients with tic douloureux there are varying degrees of demyelination in the dorsal root. This overall evidence suggests that in tic douloureux there is partial deafferentiation by virtue of demyelination and that any therapeutic mode which makes lack of conductance more complete will abolish paroxysms of pain. This has also been demonstrated in the peripheral nerve by injecting novacaine distal to the site of a process presumed to carry pain. It is suggested that intact fibers have to exist distal to site of pathoanatomical lesion. The question arises as how a partial demyelination or conductance block in parts of a neural complex may produce changes in threshold firing centrally. Obviously the latter has to occur for sensation of pain to be evoked.

Neurophysiological considerations: Thusfar, the evidence suggests that there is low threshold for firing in nucleus caudalis, and there is neuroanatomical evidence to suggest that in patients with tic douloureux there is a partial deafferentiation in terms of a conduction defect related to demyelination.

Experimental deafferentiation: Evidence exists from experiments described in the literature that in lesions in which there is partial or complete deafferentiation, there is change in the synaptic zone and change in the reactivity to ACH as a result of change in cholinesterase availability. It is known that there are varying degrees of concentration of cholonesterase in various segments of the neurons. The real reason for this is unknown. The possibility exists that there is dependence upon the need of hydrolysis of ACH.

In this regard, it is significant that in the multiple sclerosis plagues of demyelination, CHE is absent, suggesting decreased ability for hydrolysis of ACH and, therefore, the ability of available ACH to change reactivity. This is also the phenomenon in experiments involving undercutting of the cerebral frontal cortex, in which increased sensitivity to applied ACH has been observed. It suggests also why drugs such as that sold under the trademark Dilantin may relieve seizure as well as pain of tic douloureux, namely decresing effectiveness of ACH sensitivity with abolition of post tetanic potentiation. At any one time depending upon receptor site and the patient, ACH may act in a facilitatory or inhibitor fashion. The precise neurophysiological and biochemical relationships in any part have relevance.

In summary, the basic hypothesis embodies the concept that in tic douloureux there is peripheral demyelination or central demyelination (multiple sclerosis) and this is associated with lowered threshold of activity of interneurons centrally. This is the result of synaptic change in response to partial deafferentiation and this results in changing relationship of ACH-CHE. Nonpainful stimuli elicit release of ACH centrally, causing firing of interneurons at a level which is painful. Threshold for pain under normal circumstances exists in the cornea. Very fine hairs are not felt, slightly large hairs elicit touch and large hairs produce pain, so the system is geared to response of pain according to threshold of activity by varying stimulus and central activity. It is of interest in this regard that in the literature it has been demonstrated that after root section sensory loss can be reduced by modifying synaptic excitability with strychnine again illustrating the essential synaptic interaction in sensory experiences. In electric stimulation of the trigeminal system, synaptic changes must also change with change in pain. A similar phenomenon occurs in the spinal cord of patients with pain and multiple sclerosis. We see changing peripheral thresholds for reactivity with central stimulation over the cord; the inference is direct that this is the result of synaptic change.

The exact implications of the effect of ACH are open to consideration. ACH may not necessarily alone be biochemically producing change but its effect trans-synaptically on NE (Norepinephrine) synthesis may indeed be a prominent feature. It is known that ACH can modulate synthesis of tryosin hydroxylase trans-synaptically. Which of these systems is primarily or solely affected is not known but the distinct possibility exists that their relationships have distinct bearing on the sensitivity of the central synaptic zones in tic douloureux.

Because of these concepts, I performed percutaneous and converted permanent radio frequency stimulation of the trigeminal complex in patients with tic douloureux with and without multiple sclerosis. This abolished pain. This was based upon my experience with changing function in multiple sclerosis patients with stimulation over the spinal cord.

It seemed feasible that if there was relative loss of CHE with demyelination lesions, restoration of CHE may revert the process.

The etiology of the tic douloureux appears to reside in the peculiarity of function involing physiology and biochemistry and pharmacology of the trigeminal complex. This may indeed be similar in some respects to other areas of the nervous system. The absence of tic douloureux type pain in other areas such as the spinal cord may be explained by the anatomical relationship of the trigeminal sensory distribution. In the spinal cord there is much great opportunity for overlap, anatomically, synaptically and biochemically. Tic douloureux is therefore felt to result from a central biochemical disturbance involving ACH—CHE relationships as the result of degrees of dymyelination and deafferentiation of the central synaptic zones. Compounds reactivating CHE restore balance and can abort intractable severe attacks if given in sufficient amounts.

What is claimed is:

1. Method of alleviating the pain of tic douloureux comprising administering to a person suffering therefrom a dose of 2-formyl-1-methylpyridium oxime or a physiologically acceptable salt thereof effective to alleviate said pain of tic douloureux.

2. Method according to claim 1, in which the chloride of said oxime is administered.

* * * * *